United States Patent [19]
Croisy et al.

[11] Patent Number: 5,231,220

[45] Date of Patent: Jul. 27, 1993

[54] DERIVATIVES OF NORBORNYLANE AND OF DIMETHANODECAHYDRONAPHTHYLANE WHICH CAN BE USED FOR OBTAINING NEW POLYMERS

[75] Inventors: Jean Francois Croisy, Farschviller; Paul Grosius, Petite Rosselle, both of France

[73] Assignee: Norsolor, France

[21] Appl. No.: 884,459

[22] Filed: May 14, 1992

Related U.S. Application Data

[63] Continuation of Ser. No. 759,817, Sep. 4, 1991, abandoned, which is a continuation of Ser. No. 382,751, Jul. 20, 1989, abandoned.

[30] Foreign Application Priority Data

Jul. 22, 1988 [FR] France .................................. 88 09931

[51] Int. Cl.⁵ .............................................. C07C 9/52
[52] U.S. Cl. ................................... 560/220; 568/612; 568/665
[58] Field of Search ................. 560/220; 568/612, 665

[56] References Cited

U.S. PATENT DOCUMENTS

| | | | |
|---|---|---|---|
| 3,256,342 | 6/1966 | McGary | 560/220 |
| 3,799,972 | 3/1974 | Cowley et al. | 560/220 |
| 4,620,028 | 10/1988 | Gorman | 560/220 |
| 4,906,675 | 3/1990 | Inagaki et al. | 560/220 |

Primary Examiner—Paul J. Killos
Attorney, Agent, or Firm—Finnegan, Henderson, Farabow, Garrett & Dunner

[57] ABSTRACT

Derivatives (I) of norbornylane and of dimethanodecahydornaphthylane of formula:

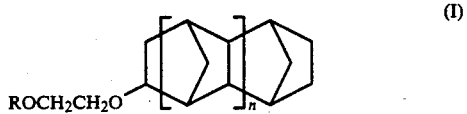

(I)

in which:
R is the hydrogen atom when n is equal to 1, or
R is the acrylol or methacryloyl radical when n is equal to 0 or 1.

Also disclosed are processes for the preparation of the derivatives (I) and their application in obtaining polymers and copolymers.

20 Claims, No Drawings

DERIVATIVES OF NORBORNYLANE AND OF DIMETHANODECAHYDRONAPHTHYLANE WHICH CAN BE USED FOR OBTAINING NEW POLYMERS

This application is a continuation of application Ser. No. 07/759,817, filed Sep. 4, 1991, now abandoned, which is a continuation of Ser. No. 07/382,751, filed Jul. 20, 1989, now abandoned.

FIELD OF THE INVENTION

The present invention relates to 2-(2-dimethanodecahdronaphthyloxy)ethanol and 2-(2-norbornyloxy)ethyl and 2-(2-dimethanodecahydronaphthyloxy)ethyl (meth)acrylates, to processes for their manufacture and to their application to the synthesis of new polymers.

DESCRIPTION OF THE INVENTION

The first subject of the present invention is new derivatives of norbornylane and of dimethanodecahydronaphthylane which have the formula:

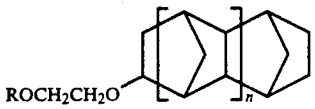
(I)

in which:
R is the hydrogen atom when n is equal to 1, or
R is the acryloyl or methacryloyl radical when n is equal to 0 or 1.

At ambient temperature, the derivatives (I) are colorless or pale yellow, relatively viscous liquids. They are miscible with many organic solvents such as aliphatic and aromatic hydrocarbons, alcohols and ketones, for example cyclohexane, xylene, ethanol and methyl isobutyl ketone. They form an emulsion with water.

2-(2-Dimethanodecahydronaphthyloxy)ethanol may be prepared in various ways. It is preferably prepared by reaction of dimethanodecahydronaphthalene with ethylene glycol in the presence of an acidic catalyst, for example a Bronsted acid such as sulfuric acid or para-toluene-sulfonic acid, or a Lewis acid such as the complexes of boron trifluoride or of aluminum trichloride or of an ion exchange resin such as sulfonic or perfluorosulfonic resins. This reaction is performed at a temperature which is generally from 40° C. to 130° C.

The derivatives (I) containing a (meth)acrylic functional group are prepared either by direct esterification or by transesterification.

The transesterification may be carried out using an alkyl(meth)acrylate such as methylmethacrylate or ethylacrylate, with the corresponding alcohol, namely 2-(2-norbornyloxy)ethanol or 2-(2-dimethanodecahydronaphthyloxy)ethanol, respectively, according to whether n is equal to 0 or 1. It is generally carried out in the presence of at least one polymerization inhibitor in a proportion of at least 200 ppm and of at least one transesterification catalyst in a proportion of at least 0.3% by weight relative to the alcohol, at a temperature which is generally from 60° C. to 140° C.

The direct esterification is carried out by reacting (meth)acrylic acid with 2-(2-norbornyloxy)ethanol or 2-(2-dimethanodecahydronaphthyloxy)ethanol respectively, depending on whether n is equal 0 or 1. It is generally performed in the presence of at least one polymerization inhibitor in a proportion of at least 200 ppm and of at least one esterification catalyst in a proportion of at least 0.3% by weight relative to the alcohol, at a temperature which is generally from 40° C. to 100° C. The reaction is perferably performed in the presence of at least one organic solvent, for example cyclohexane, heptane or toluene, in order to remove the water formed by azeotropic distillation.

Among the polymerization inhibitors which are suitable for the above mentioned transesterification and esterification processes there may be mentioned phenothiazine, tert-butylcatechol, hydroquinone methyl ether, hydroquinone, methylene blue and copper and iron sulfates.

Alkyl titanates such as ethyl titanate, and zirconium complexes such as zirconium tetraacetylacetonate may be employed as a transesterification catalyst. Suitable catalysts for direct esterification are acids such as para-toluenesulfonic acid, methanesulfonic acid or sulfuric acid.

The derivatives (I) according to the invention have various applications.

2-(2-Dimethanodecahydronaphthyloxy)ethanol is essentially a reaction intermediate used especially for preparing the derivatives (I) containing a (meth)acrylic functional group. These can be polymerized or copolymerized with other ethylenically unsaturated monomers such as ethylene, vinylaromatic hydrocarbons such as styrene, vinyltoluene or alpha-methylstyrene, and acrylic or methacrylic compounds such as alkyl (meth)acrylates whose alkyl group contains from 1 to 20 carbon atoms, (meth)acrylamides, dialkylaminoalkyl (meth)acrylates and their quarternary salts and, generally, any ethylenically unsaturated monomers capable of copolymerizing by a radical mechanism under the effect of a free-radical generator such as microwaves, beta, gamma or ultraviolet radiation or a chemical initiator such as a persulfate, peroxide, hydroperoxide or diazo compound.

Thus, a second subject of the present invention resides in a polymer containing in its chain at least one unit derived from a 2-(2-norbornyloxy)ethyl or 2-(2-dimethanodecahydronaphthyloxy)ethyl (meth)acrylate and, where appropriate, at least one unit derived from another ethylenically unsaturated monomer such as described above. In the case of copolymers, the polymerization conditions will be chosen as close as possible to those usually employed for the polymerization of the ethylenically unsaturated comonomer, namely for example:

a temperature of from 140° C. to 300° C. and a pressure of from 1,000 to 3,000 bars, approximately, when this monomer is ethylene, a temperature of from 30° C. to 90° C., approximately, when this comonomer is an acrylic or methacrylic compound, a temperature of from 80° C. to 200° C., approximately, when this comonomer is a vinylaromatic hydrocarbon.

The examples given below by way of guidance will enable the invention to be better understood.

EXAMPLE 1

Into a jacketed reactor supporting a mechanical stirrer and a condenser and fitted with a device for measuring temperature, were introduced 62.1 g of ethylene glycol and 10.7 g of an ion exchange resin by the trade name of Amberlyst 15. As soon as the temprature in the reactor reached 90° C., 160 g of dimethanodecahydronaphthalene were added gradually over 4 hours.

The reaction was carried out at a temperature of 90° C. After reacting for 7 hours the catalyst was filtered off and the reaction mixture was distilled. 2-(2-Dimethanodecahydronaphthyloxy)ethanol was obtained at 175° C. at $1.07 \times 10^3$ Pa (8 mm Hg) in a 96.1% yield. It was in the form of a colorless viscous liquid with a refractive index $n_D^{20}$ equal to 1.5218.

Carbon 13 NMR and infrared spectra confirmed that a mixture of the exo (71%) and endo (29%) isomers of 2-(2-dimethanodecahydronaphthyloxy)ethanol had been obtained.

EXAMPLE 2

The following charge was introduced into an apparatus identical with that described in Example 1 and supporting a distillation column with a reflux head permitting an azeotropic distillation:

| | |
|---|---|
| methacrylic acid (g) | 172.2 |
| 2-(2-dimethanodecahydronaphthyloxy)-ethanol (g) | 110 |
| hydroquinone methyl ether (g) | 0.14 |
| copper sulfate (g) | 0.17 |
| para-toluenesulfonic acid (g) | 6.9 |
| cyclohexane (ml) | 200 |

The reaction was performed at 80° C. at atmospheric pressure. After reacting for 4 hours the excess acid was neutralized and the cyclohexane was removed under vacuum. 2-(2-Dimethanodecahydronaphthyloxy)ethyl methacrylate was obtained in a 97% yield, the product obtained having a purity of 93% (measured by gas phase chromatography).

The product obtained was a pale yellow liquid.

EXAMPLE 3

The following charge was introduced into an apparatus identical with that described in Example 2:

| | |
|---|---|
| acrylic acid (g) | 114.1 |
| 2-(2-dimethanodecahydronaphthyloxy)-ethanol (g) | 111 |
| hydroquinone methyl ether (g) | 0.11 |
| copper sulfate (g) | 0.14 |
| methanesulfonic acid (g) | 5.76 |
| cyclohexane (ml) | 200 |

The reaction was performed at 80° C. at atmospheric pressure. After reacting for 4 hours the excess acid was neutralized and the cyclohexane was removed. 2-(2-Dimethanodecahydronaphthyloxy)ethyl acrylate is obtained in a 95% yield, the product obtained having a purity of 94% (measured by gas phase chromatography). The product obtained is a pale yellow liquid.

EXAMPLE 4 a) Preparation of exo 2-(2-norbornyloxy)ethanol 94 g of norbornene were introduced into an apparatus identical with that described in Example 1 and were preheated. Once the norbornene was liquid, 93 g of ethylene glycol and 10.6 g of Amberlyst 15 resin were added. A twophase mixture was then obtained. After reacting for 5 hours the resin was filtered off and the reaction mixture was distilled. Exo 2-(2-norbornyloxy)ethanol was obtained at 127° C. at $3.33 \times 10^3$ Pa (25 mm Hg) in an 83% yield. It was in the form of a colorless liquid whose refractive index was equal to 1.4788 at 20° C. and whose density was equal to 1.04 g/cm³ at 23.5° C.

b) Preparation of exo 2-(2-norbornyloxy)ethyl methacrylate:

The following charge was introduced into an apparatus identical with that of Example 2:

| | |
|---|---|
| methyl methacrylate (g) | 200 |
| exo 2-(2-norbornyloxy)ethanol (g) | 156 |
| hydroquinone methyl ether (g) | 0.16 |
| ethyl titanate (g) | 2.74 |

The reaction was performed at 90° C. After reacting for 8 hours the excess methyl methacrylate was distilled off, followed by 2-(2-norbornyloxy)ethyl methacrylate at 135° C. at $0.8 \times 10^3$ Pa (6 mm Hg).

The reaction yield was 84.9%. 2-(2-norbornyloxy)ethyl methacrylate was in the form of a colorless viscous liquid with a refractive index of 1.4767 at 20° C.

EXAMPLE 5

The following charge was introduced into an apparatus identical with that of Example 2:

| | |
|---|---|
| ethyl acrylate (g) | 200 |
| exo 2-(2-norbornyloxy)ethanol (g) | 156 |
| zirconium tetraacetylacetonate (g) | 1.46 |
| hydroquinone methyl ether (g) | 0.16 |

The reaction was performed at 90° C. After reacting for 8 hours the excess ethyl acrylate was distilled off and the exo 2-(2-norbornyloxy)ethyl acrylate was obtained at 125° C. at $0.8 \times 10^3$ pa (6 mm Hg) in a 98% yield. It was in the form of a colorless liquid with a refractive index equal to 1.4775 at 20° C.

Endo 2-(2-norbornyloxy)ethyl acrylate and methacrylate were obtained as a mixture with exo 2-(2-norbornyloxy)ethyl acrylate and methacrylate respectively, by using the operating procedures described in Examples 4 and 5 above and employing endo 2-(2-norbornyloxy)ethanol as starting material. The latter was obtained by reduction of the norbornylane ethylene ketal using the LiAlH$_4$-AlCl$_3$ system (Can. J. Chem. 44/13, 1547–50, (1966)).

What is claimed is:

1. A derivative of norbornylane and of dimethanodecahydronaphthylane of formula (I):

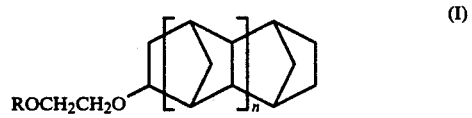

in which:
R is the hydrogen atom when n is equal to 1,
or R is the acryloyl or methacryloyl radical when n is equal to 0 or 1.

2. A process for the preparation of a derivative of formula (I) according to claim 1, for which n is equal to 1 and R is the hydrogen atom, which comprises reacting dimethanodecahydronaphthalene and ethylene glycol in the presence of an acidic catalyst.

3. The process according to claim 2, wherein the said reaction is performed at a temperature from 40° C. to 130° C.

4. A process for the preparation of the derivative (I) according to claim 1, for which R is the acryloyl or methacryloyl radical and n is equal to 0 or 1, which comprises reacting an alkyl methacrylate with the corresponding alcohol, of 2-(2-norbornyloxy)ethanol when n is equal to 0, or 2-(2-dimethanodecahydronaphthyloxy)ethanol when n is equal to 1.

5. The process according to claim 4, wherein the reaction is performed at a temperature from 60° C. to 140° C.

6. A process for the preparation of the derivatives of formula (I) according to claim 1, for which R is the acryloyl or methacryloyl radical and n is equal to 0 or 1, which comprises reacting (meth)acrylic acid with 2-(2-norbornyloxy)ethanol when is equal to 0, or 2-(2-dimethanodecahydronaphthyloxy)ethanol when n is equal to 1.

7. The process according to claim 6, wherein the reaction is performed in the presence of an organic solvent.

8. The process according to claim 6, wherein the reaction is performed at a temperature from 40° C. to 100° C.

9. The process according to claim 8, wherein the reaction is performed in the presence of at least one polymerization inhibitor.

10. The process according to claim 7, wherein the reaction is performed in the presence of at least one polymerization inhibitor.

11. The process according to claim 6, wherein the reaction is performed in the presence of at least one polymerization inhibitor.

12. The process according to claim 5, wherein the reaction is performed in the presence of at least one polymerization inhibitor.

13. The process according to claim 4, wherein the reaction is performed in the presence of at least one polymerization inhibitor.

14. The process according to claim 8, wherein the reaction is performed in the presence of at least one catalyst.

15. The process according to claim 7, wherein the reaction is performed in the presence of at least one catalyst.

16. The process according to claim 6, wherein the reaction is performed in the presence of at least one catalyst.

17. The process according to claim 5, wherein the reaction is performed in the presence of at least one catalyst.

18. The process according to claim 4, wherein the reaction is performed in the presence of at least one catalyst.

19. A polymer containing in its chain at least one unit derived from a 2-(2-norbornyloxy)ethyl or 2-(2-dimethanodecahydronaphthyloxy)ethyl (meth)acrylate.

20. The polymer according to claim 19 also containing in its chain at least one unit derived from another ethylenically unsaturated monomer selected from the group consisting of ethylene, a vinylaromatic hydrocarbon, an acrylic compound, and a methacrylic compound.

* * * * *